US00PP35182P2

(12) United States Plant Patent
Rupp

(10) Patent No.: US PP35,182 P2
(45) Date of Patent: May 23, 2023

(54) ***DIANTHUS* PLANT NAMED 'KLEDG22634'**

(50) Latin Name: ***Dianthus caryophyllus* L.**
Varietal Denomination: KLEDG22634

(71) Applicant: Klemm+Sohn GmbH & Co. KG, Stuttgart (DE)

(72) Inventor: Judith Rupp, Stuttgart (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/972,743

(22) Filed: Oct. 25, 2022

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./263.1, 272, 273
See application file for complete search history.

(56) References Cited

PUBLICATIONS

Walters Garden, citation for 'Paint the Town Fancy'. 2021. https://www.waltersgardens.com/photo_essay.php?ID=428&view=Slideshow. 5 pages. (Year: 2021).*

* cited by examiner

*Primary Examiner* — Karen M Redden
(74) *Attorney, Agent, or Firm* — Weatherly IP Solutions, LLC; James M. Weatherly

(57) ABSTRACT

A new *Dianthus* plant designated 'KLEDG22634' particularly distinguished by semi-double, dark pink flowers with purple centers, and an upright habit, is disclosed.

1 Drawing Sheet

Genus and species: *Dianthus caryophyllus* L.
Variety denomination: 'KLEDG22634'.

BACKGROUND OF THE NEW PLANT

The present invention comprises a new and distinct variety of *Dianthus*, botanically known as *Dianthus caryophyllus* L., and hereinafter referred to by the variety name 'KLEDG22634'. 'KLEDG22634' originated from a naturally-occurring, whole plant mutation from the *Dianthus* parent 'KLEDG12163' (U.S. Plant Pat. No. 24,707) in a greenhouse in May 2018 in Stuttgart, Germany.

In August 2018, 'KLEDG22634' was first vegetatively propagated by vegetative stem cuttings in Stuttgart, Germany. 'KLEDG22634' was found to reproduce true to type in successive generations of asexual propagation in Stuttgart, Germany via vegetative cuttings.

SUMMARY

The following are the most outstanding and distinguishing characteristics of 'KLEDG22634' when grown under normal horticultural practices in Stuttgart, Germany.

1. Semi-double pink flowers with purple centers; and
2. An upright habit.

DESCRIPTION OF THE PHOTOGRAPH

This new *Dianthus* plant is illustrated by the accompanying photograph of a 30-week-old plant taken in September 2021 and grown outdoors in Stuttgart, Germany. The colors shown are as true as can be reasonably obtained by conventional photographic procedures. The photograph is a whole plant photo of 'KLEDG22634' and shows the foliage, buds, and flowers.

DESCRIPTION

The following detailed descriptions set forth the distinctive characteristics of 'KLEDG22634'. The data which define these characteristics were collected from asexual reproductions carried out in Stuttgart, Germany. Data was collected in May 2019 from plants that were 7-months-old and grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus* L.
- *Designation*.—'KLEDG22634'.
- *Type*.—Pot carnation.

Parentage: Naturally-occurring, whole plant mutation of *Dianthus* parent 'KLEDG12163' (U.S. Plant Pat. No. 24,707).

Plant:
- *Propagation type*.—Vegetative stem cuttings, terminal cuttings.
- *Time to produce a rooted young plant*.—10 to 14 days.
- *Root description*.—Fine; young roots are RHS 161D (Greyed-Yellow) and mature roots are RHS 199C (Grey-Brown).
- *Rooting habit shape*.—Lanceolate.
- *Plant form*.—Upright.
- *Plant height*.—15.0 cm to 17.0 cm.
- *Plant diameter or spread*.—22.0 cm to 25.0 cm.

*Hardiness*.—Winter-hardy (tested under conditions in Germany, up to −10° C.).

Lateral branches/stems:

*Shape of the branch in cross-section*.—Slightly angular.

*Hollowness of the branch*.—Absent.

*Length*.—7.0 cm to 10.0 cm.

*Diameter*.—4.0 cm to 7.0 cm.

*Internode length*.—2.0 cm to 3.0 cm.

*Node length*.—0.2 cm to 0.4 cm.

*Node diameter*.—0.2 cm to 0.4 cm.

*Texture*.—Smooth.

*Color*.—RHS 146B (Yellow-Green).

Foliage:

*Arrangement*.—Opposite.

*Length*.—4.0 cm to 5.0 cm.

*Width*.—0.3 cm to 0.5 cm.

*Shape*.—Lanceolate.

*Apex*.—Acute.

*Base*.—Obtuse.

*Margin*.—Entire.

*Texture* (*both upper and lower surfaces*).—Smooth.

*Cross-section of the leaf*.—Moderately concave.

*Curvature of the leaf*.—Weakly recurved.

*Glaucosity of the leaf*.—Weak.

*Leaf color, immature, both surfaces*.—RHS 138A (Green).

*Leaf color, mature, both surfaces*.—RHS 137A (Green).

*Venation pattern*.—Absent.

Flowers:

*Flower type*.—Semi-double.

*Fragrance*.—Present.

*Position of the flowers compared to the foliage of the plant*.—Moderately above.

*Natural flowering season*.—Spring to Autumn.

*Flower longevity on the plant*.—14 to 18 days.

Buds:

*Length*.—0.5 cm to 1.5 cm.

*Diameter*.—0.3 cm to 0.4 cm.

*Shape*.—Elliptic.

*Color*.—RHS 138A (Green).

Corolla:

*Quantity of petals and arrangement*.—7 to 13 and arranged in several whorls.

*Corolla height*.—0.8 cm to 1.5 cm.

*Petal length*.—1.8 cm to 2.5 cm.

*Petal width*.—1.0 cm to 1.5 cm.

*Petal shape*.—Spoon-shaped.

*Petal apex*.—Obtuse.

*Petal base*.—Acute.

*Petal margin*.—Serrated.

*Petal texture* (*both upper and lower surfaces*).—Smooth.

*Petal color*.—Immature: Upper surface: RHS 68B (Red-Purple) with RHS N79C (Purple). Mature: Upper surface: RHS 68B (Red-Purple) with RHS N79C (Purple).

*Calyx*.—Quantity of sepals: Composed of 5 sepals. Calyx height: 0.8 cm to 1.5 cm. Calyx diameter (at the apex): 0.4 cm to 0.6 cm. Sepal texture (both upper and lower surfaces): Smooth. Sepal color: Upper surface: RHS 137A (Green). Lower surface: RHS 137D (Green).

Peduncles:

*Length*.—5.0 cm to 8.0 cm.

*Diameter*.—0.2 cm.

*Strength*.—Moderate.

*Texture*.—Smooth.

*Color*.—RHS 146B (Yellow-Green).

Reproductive organs:

*Stamens*.—Quantity per flower: Moderate. Filament length: 0.5 cm to 0.8 cm. Anther length: 0.1 cm. Anther diameter: 0.05 cm. Anther color: RHS 155B (White).

*Pistils*.—Not observed.

Fruit and seed set: Observed but no information is available.

Disease and pest/insect resistance: No disease and pest/insect resistance observed.

COMPARISON WITH PARENTAL LINE AND KNOWN VARIETY

'KLEDG22634' is distinguished from the parental line as described in Table 1.

TABLE 1

Comparison with Parental Line

| Characteristic | 'KLEDG22634' | Mutation Parent 'KLEDG12163' |
|---|---|---|
| Petal color, upper surface | RHS 68B (Red-Purple) with RHS N79C (Purple) | RHS N79B and RHS N74D |

'KLEDG22634' can be compared to the commercial *Dianthus* variety 'KLEDG18305' (U.S. Plant Pat. No. 31,019). Differences between the varieties are described in Table 2.

TABLE 2

Comparison with Similar Variety

| Characteristic | 'KLEDG22634' | 'KLEDG18305' |
|---|---|---|
| Flower type | Semi-double | Single |
| Petal color, upper surface | RHS 68B (Red-Purple) with RHS N79C (Purple) | RHS 49A (Red); in the summer, has red ring of RHS 42A (Red) |

I claim:

1. A new and distinct variety of *Dianthus* plant designated 'KLEDG22634' as illustrated and described herein.

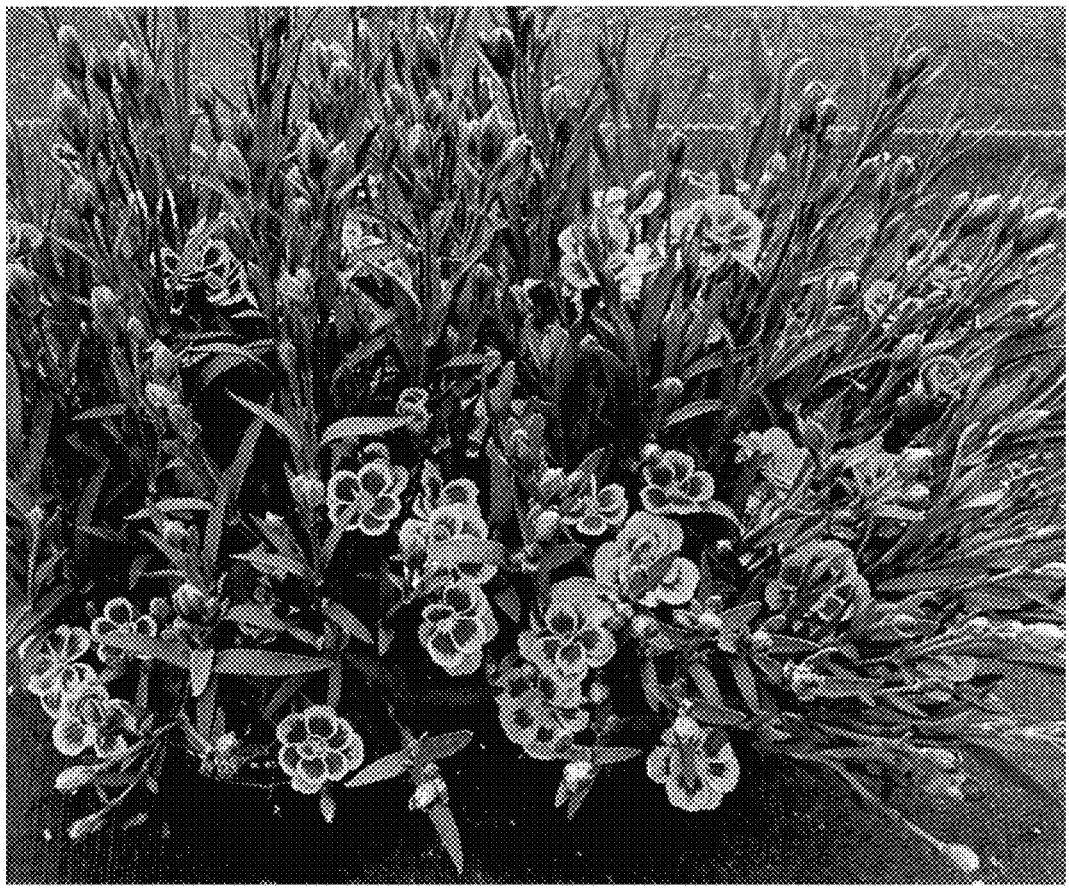

* * * * *